(12) United States Patent
Hwang et al.

(10) Patent No.: US 7,805,184 B2
(45) Date of Patent: Sep. 28, 2010

(54) PORTABLE BODY FAT MEASUREMENT DEVICE AND OPTICAL SENSOR MODULE OF THE DEVICE

(75) Inventors: In Duk Hwang, Suwon-si (KR); Kun Soo Shin, Seongnam-si (KR); Kun Kook Park, Suwon-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 491 days.

(21) Appl. No.: 11/797,199

(22) Filed: May 1, 2007

(65) Prior Publication Data

US 2007/0293768 A1    Dec. 20, 2007

(30) Foreign Application Priority Data

May 2, 2006    (KR) .................. 10-2006-0039638

(51) Int. Cl.
A61B 6/00    (2006.01)
(52) U.S. Cl. .................................... 600/476
(58) Field of Classification Search ............ 600/310, 600/473, 476; 356/39–41
See application file for complete search history.

(56) References Cited

U.S. PATENT DOCUMENTS

| | | | |
|---|---|---|---|
| 5,014,713 A | 5/1991 | Roper et al. | |
| 5,490,506 A * | 2/1996 | Takatani et al. | 600/309 |
| 5,598,842 A * | 2/1997 | Ishihara et al. | 600/322 |
| 6,078,833 A | 6/2000 | Hueber | |
| 6,285,904 B1 | 9/2001 | Weber et al. | |
| 6,315,955 B1 | 11/2001 | Klein | |
| 6,584,340 B1 * | 6/2003 | Horiuchi et al. | 600/473 |
| 7,251,513 B2 | 7/2007 | Kondoh et al. | |
| 2002/0183624 A1 | 12/2002 | Rowe et al. | |
| 2004/0111035 A1 | 6/2004 | Kondoh et al. | |
| 2007/0293767 A1 | 12/2007 | Hwang et al. | |

FOREIGN PATENT DOCUMENTS

| | | |
|---|---|---|
| EP | 0819970 | 1/1998 |
| EP | 0819970 A1 | 1/1998 |
| EP | 1396227 | 3/2004 |
| EP | 1396227 A1 | 3/2004 |
| EP | 1520514 | 4/2005 |

(Continued)

OTHER PUBLICATIONS

Korean Office Action for corresponding Korean Application No. 10-2006-0039638 dated Jul. 6, 2007.

(Continued)

Primary Examiner—Eric F Winakur
Assistant Examiner—Michael T Rozanski
(74) Attorney, Agent, or Firm—Staas & Halsey LLP

(57) ABSTRACT

A portable body fat measurement device includes: a light source unit having at least two top view light sources and a guide unit perpendicularly guiding an optical signal generated in the top view light sources to determine a measurement point where body fat is measured; an optical detection unit detecting a scattered optical signal to transform into an electrical signal, the scattered optical signal being generated by a scattering of the optical signal irradiated to the measurement point; and a signal processing unit processing the electrical signal and calculating body fat information, wherein the at least two top view light sources and the optical detection unit are horizontally arranged.

19 Claims, 5 Drawing Sheets

FOREIGN PATENT DOCUMENTS

| | | |
|---|---|---|
| EP | 1520514 A1 | 4/2005 |
| EP | 1634533 | 3/2006 |
| EP | 1634533 A1 | 3/2006 |
| JP | 2000-155091 | 6/2000 |
| JP | 2000-237195 | 9/2000 |
| JP | 2002-27051 | 1/2002 |
| JP | 2003-265440 | 9/2003 |
| JP | 2004-350836 | 12/2004 |
| KR | 10-2001-0008540 | 2/2001 |
| KR | 2001-0099267 | 11/2001 |
| KR | 10-2001-0106960 | 12/2001 |
| KR | 10-2002-0088833 | 11/2002 |
| KR | 10-2004-0101043 | 12/2004 |
| KR | 10-2004-0106833 | 12/2004 |
| KR | 10-2005-0103355 | 10/2005 |
| KR | 10-2005-0105783 | 11/2005 |
| WO | 01/28416 | 4/2001 |
| WO | WO01/28416 A1 | 4/2001 |

OTHER PUBLICATIONS

Office Action dated Aug. 6, 2008 for related U.S. Appl. No. 11/797,198.
Office Action dated Sep. 21, 2009 for related U.S. Appl. No. 11/797,198.
Final Office Action dated Jan. 7, 2010 for related U.S. Appl. No. 11/797,198.
Office Action dated Mar. 16, 2010 for related U.S. Appl. No. 11/797,198.
Notice of Allowance dated Apr. 5, 2010 for related U.S. Appl. No. 11/797,198.
European Search Report for corresponding European Patent Application No. 07075331.4 dated Apr. 20, 2010 (7 pgs) (in English).
Korean Office action Jul. 27, 2007, issued in Korean Pat. No. 10-2006-0044953.
European search report Aug. 9, 2007 issued in European pat No. 07107810.9 (in english).
Office actions mailed Jun. 18, 2008, Nov. 24, 2008, and Jul. 6, 2009 and advisory action mailed Feb. 20, 2009 in copending U.S. Appl. No. 11/797,198.

* cited by examiner

FIG. 2
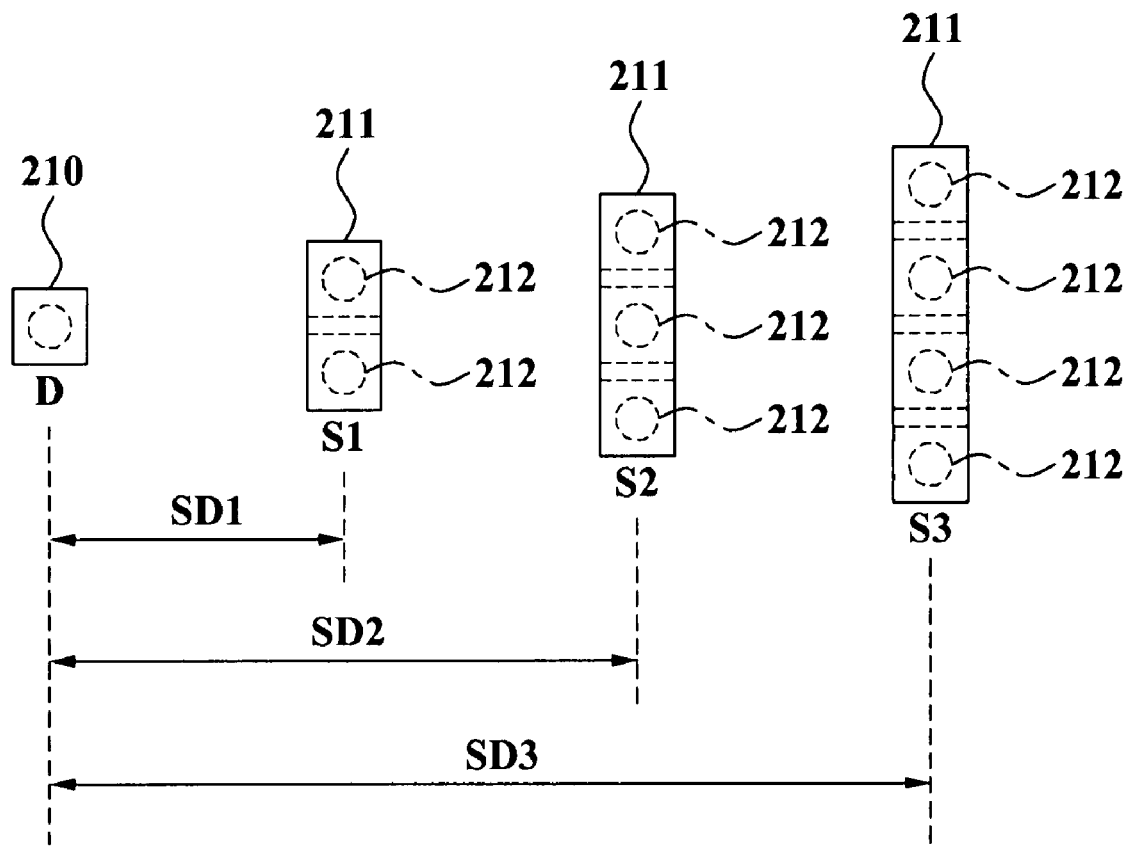
(a)
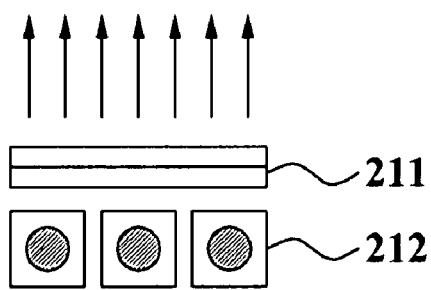
(b)

FIG. 4
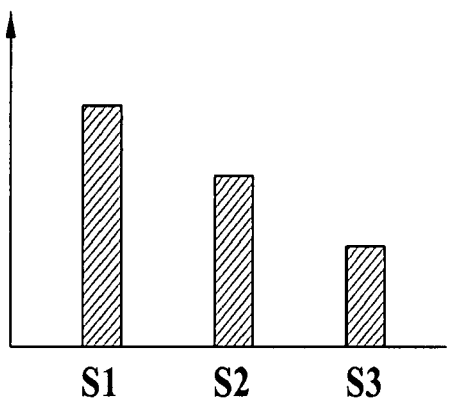
(a)
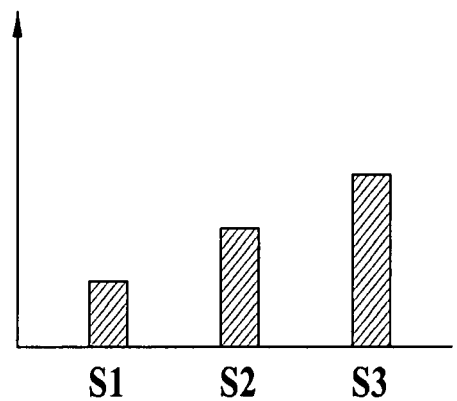
(b)

PORTABLE BODY FAT MEASUREMENT DEVICE AND OPTICAL SENSOR MODULE OF THE DEVICE

CROSS-REFERENCE TO RELATED APPLICATIONS

This application claims the benefit of Korean Patent Application No. 10-2006-0039638, filed on May 2, 2006, in the Korean Intellectual Property Office, the disclosure of which is incorporated herein by reference.

BACKGROUND

1. Field

The present invention relates to a portable body fat measurement device having a top-view light source and an optical sensor module of the portable body fat measurement device, and more particularly to a portable body fat measurement device which enters a light outputted from a top view light source in a measurement point and calculates body fat information by using a scattered light scattered from the measurement point, and an optical sensor module of the portable body fat measurement device.

2. Description of the Related Art

Health and beauty are critical issues for people living in modern society, accordingly a well-being trend seeking a healthy and enjoyable life is currently booming. One criterion for health estimation is measuring an obesity rate. There are various methods of measuring the obesity rate, and a body fat ratio is usually one of the criteria for measuring the obesity rate. Also, the body fat ratio may be one criterion for people on a diet for beauty purposes.

The methods of measuring a body fat ratio consists of a body average density measurement measuring weight in the water, a skinfold test calculating the body fat ratio by measurement thickness of fat in a specific point of a body, a body impedance analysis calculating the body fat ratio by measuring a resistance in a body by flowing a weak current in the body, a weight and waist relation table measuring the body fat ratio by using a weight and a waist size, and the like. However these methods need mostly complicated equipment and are inaccurate when measuring the body fat ratio.

Currently, a body fat measurement method using a light capable of readily and accurately measuring body fat, is disclosed. A body fat measurement device using the light is based on a theory that when a light emitted from a light source is irradiated at a measurement point of a body, backward-scattering occurs in the body, and subsequently, a body fat is measured by measuring a scattered optical signal using an optical detector. The body fat measurement device using the light has a defect in that the light source is generally too large to be adopted into a portable device, and when the device is miniaturized, accuracy of the body fat measurement device may not be guaranteed since the accuracy of the body fat measurement device depends on a light irradiated dimension and an optical volume. Accordingly, there is a need for a portable body fat measurement device which readily and accurately measures thickness of body fat for a user.

SUMMARY

Additional aspects and/or advantages will be set forth in part in the description which follows and, in part, will be apparent from the description, or may be learned by practice of the invention.

In an aspect of the present invention, a portable body fat measurement device and an optical sensor module in the device which may be installed in a portable terminal, e.g. a mobile communication terminal, are provided in which a thickness of the optical sensor module is minimized since a top view light source type light of a surface mount is used as the optical sensor module.

In an aspect of the present invention, a portable body fat measurement device and an optical sensor module in the device are provided in which a thickness of the optical sensor module is minimized and a sufficient optical volume for measuring a thickness of a body fat is enabled since the optical sensor module is configured by horizontally arranging at least two light sources and an optical detection unit.

In an aspect of the present invention, a portable body fat measurement device and an optical sensor module in the device are also provided which minimize a decrease of optical power since an irradiation angle of a light outputted from a top view light source is limited via a guide unit, e.g., a prism sheet and the like, so that the light is perpendicularly irradiated in a measurement point.

In an aspect of the present invention, a portable body fat measurement device and an optical sensor module in the device are provided which minimize a measurement error of a thickness of body fat, which is caused by absorption of a scattered light by hemoglobin (Hb), by outputting a message requesting a change of a measurement point when an optical detection unit receiving a scattered light backscattered from the measurement point is above a blood vessel.

According to an aspect of the present invention, there is provided a portable body fat measurement device that includes: a light source unit having at least two top view light sources and a guide unit perpendicularly guiding an optical signal generated in the top view light sources for a measurement point where body fat is measured; an optical detection unit detecting a scattered optical signal to transform into an electrical signal, the scattered optical signal being generated by a scattering of the optical signal irradiated to the measurement point; and a signal processing unit processing the electrical signal and calculating body fat information, wherein the at least two top view light sources and the optical detection unit are horizontally arranged.

According to another aspect of the present invention, there is provided an optical sensor module included in a body fat measurement device, wherein the module includes: a light source unit having at least two top view light sources and a guide unit perpendicularly guiding an optical signal generated in the top view light sources for a measurement point where body fat is measured; an optical detection unit detecting a scattered optical signal to transform into an electrical signal, wherein the at least two top view light source and the optical detection unit are horizontally arranged, the electrical signal is supplied to a predetermined signal processing unit, and the signal processing unit receives the electrical signal to calculate body fat information in the measurement point.

In an aspect of the present invention, the mobile terminal may be one of a personal digital assistant (PDA), a portable game device, an MP3 player, a personal multimedia player (PMP), a Digital Multimedia broadcasting (DMB) terminal, or a notebook.

In an aspect of the present invention, optical detection unit of the portable body fat measurement device includes an optical-electrical transducing element transforming an optical signal into an electrical signal.

In an aspect of the present invention, the optical detection unit of the optical sensor module includes an optical-electrical transducing element transforming an optical signal into an electrical signal.

In an aspect of the present invention, in the optical sensor module, at least one light source unit outputs an optical signal having a wavelength between approximately 600 and 800 nm.

In an aspect of the present invention, in the portable body fat measurement device, at least one light source unit outputs a light having a wavelength between approximately 600 and 950 nm.

In an aspect of the present invention, in the optical sensor module, at least one light source unit outputs an optical signal having a wavelength between approximately 600 and 950 nm.

BRIEF DESCRIPTION OF THE DRAWINGS

These and/or other aspects and advantages will become apparent and more readily appreciated from the following description of the embodiments, taken in conjunction with the accompanying drawings of which:

FIG. 2(a) is a diagram illustrating a top view of an optical sensor module in a portable body fat measurement device according to an embodiment of the present invention, and FIG. 2(b) is a diagram illustrating a structure and a shape of the top view light sources and the guide unit in accordance with an embodiment of the present invention;

FIG. 4 illustrates histograms showing a volume of operation current of an optical sensor module and a volume of a scattered light scattered from a measurement point according to an embodiment of the present invention.

DETAILED DESCRIPTION OF THE EMBODIMENTS

Figure 1:
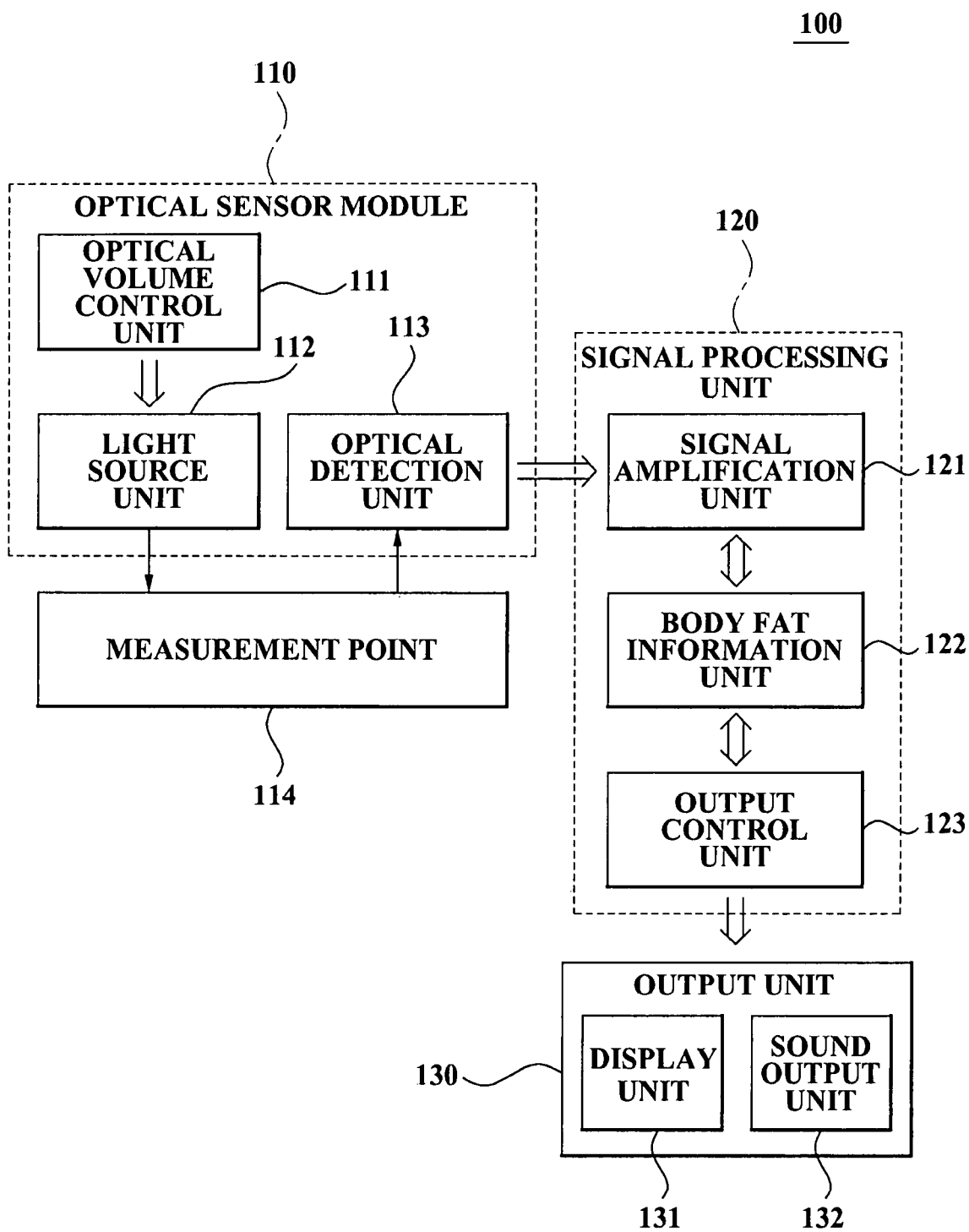
FIG. 1 is a block diagram illustrating a configuration of a portable body fat measurement device according to an embodiment of the present invention.

Reference will now be made in detail to embodiments of the present invention, examples of which are illustrated in the accompanying drawings, wherein like reference numerals refer to the like elements throughout. The embodiments are described below to explain the present invention by referring to the figures.

A portable body fat measurement device may include one of a mobile terminal, e.g., a personal digital assistant (PDA), a portable game device, an MP3 player, a personal multimedia player (PMP), a Digital Multimedia broadcasting (DMB) terminal, and a notebook. Namely, the portable body fat measurement device may be embodied as an optical sensor module, according to an embodiment of the present invention, that is included as one configuration of the mobile terminal. Also, the portable body fat measurement device may not be installed in the mobile terminal, but rather may be designed to have an independent configuration from the mobile terminal.

Also, a measurement point 114 used in the current invention includes a human body and a bioprosthetic tissue having a similar property with respect to a property of the human body. The portable body fat measurement device and the optical sensor module in the device may be used for measuring a thickness of body fat included in the human body and in the bioprosthetic tissue.

FIG. 1, numeral 100, is a block diagram illustrating a configuration of a portable body fat measurement device according to an embodiment of the present invention.

The portable body fat measurement device according to the present invention includes an optical sensor module 110, a signal processing unit 120 and an output unit 130. The optical sensor module 110 includes an optical volume control unit 111, a light source unit 112 and an optical detection unit 113. The signal processing unit 120 includes a signal amplification unit 121, a body fat information unit 122 and an output control unit 123. The output unit 130 includes a display unit 131 and a sound output unit 132.

The light source unit 112 of the optical sensor module 110 includes a guide unit 211 perpendicularly guiding at least two top view light sources outputting a light having a predetermined dimension and a light irradiated from the two top view light sources.

The top view light sources may be one of a point light source or a surface light source, and the point light source or the surface light source includes a light emitting diode (LED). The guide unit 211 guides the light irradiated from the two top view light sources to be perpendicularly irradiated to a measurement point 114, and the guide unit 211 may be a prism sheet. A structure and a shape of the top view light sources and the guide unit 211 will be described in detail by referring to FIG. 2(b).

FIG. 2(a) is a diagram illustrating a top-view of an optical sensor module in a portable body fat measurement device according to an embodiment of the present invention.

In FIG. 2(a), a top view of the optical detection unit 210 of the optical sensor module 110 and the light source unit 112 are illustrated. Depending upon the embodiment of the present invention, with respect to the light source unit 112, at least two light source units may be utilized for measuring the thickness of body fat, and at least three light source units may be utilized for comparatively more accurate measurement. As a number of the light source units increases, a reference of a scattered light that may be used for the measurement of the body fat for the measurement point 114 increases, and therefore, accuracy of a measurement result may be improved.

Examples of three light source units S1, S2 and S3 are illustrated in FIG. 2(a).

The at least two light source units 212 and a optical detection unit 210 are horizontally arranged, such as are illustrated in FIG. 2(a), and each of the light source units S1, S2, and S3 is horizontally arranged apart from the optical detection unit 210 by spaced distances SD1, SD2 and SD3, respectively.

The light source units S1, S2, and S3 include a top view light source 212 and a guide unit 211. At least one top view light source 212 may be established in each of the light source units S1, S2, and S3, such as are illustrated in FIG. 2(a), and each of the light source units S1, S2, and S3 are horizontally arranged with respect to the optical detection unit 210 and include at least one top view light source 212. A number and a location of the top view light source 212 may be variously embodied by those skilled in the art. The top view light source 212 may be one of a point light source or a surface light source, both of which may include an LED.

The guide unit 211 perpendicularly guides the light irradiated from the top view light sources to be irradiated toward a measurement point 114. Since a general top-view LED has a large radiation angle, an intensity of a light which is outputted to a perpendicular direction tends to decrease. Therefore, the guide unit 211 may minimize the decrease of the light by reducing the radiation angle of the light from the top view LED and guiding the light in the measurement point 114 in a perpendicular direction. For the above operation, the guide unit 211 may include a prism sheet. Also, the guide unit 211 may include various units used in the art, including the prism sheet.

As described above, the light from the top view light source 212 is perpendicularly irradiated in the measurement point 114 via the guide unit 211. In this case, the light is irradiated via an entire top surface of the guide unit 211, i.e., the light is irradiated in a type of a surface light, and the irradiated light is may be as large as a dimension of the top surface of the guide unit 211.

Each of the light source units S1, S2, and S3, including the top view light source 212 and guide unit 211, is spaced apart from the optical detection unit 210 by a predetermined distance, i.e., the light source S1 is spaced apart from the optical detection unit 210 by a spaced distance SD1, the light source S2 is spaced apart from the optical detection unit 210 by a spaced distance SD2, and the light source S3 is spaced apart from the optical detection unit 210 by a spaced distance SD3. The spaced distances SD1, SD2, and SD3 may be variously established according to a threshold of the thickness of the body fat measurable in the measurement point 114. Namely, when values of the spaced distances SD1, SD2, and SD3 are increased, the threshold of the thickness of the body fat that is measurable in the measurement point 114 comparatively increases.

Also, optical volumes outputted from each of the top view light sources 212 of each of the light source units may increase according to the spaced distances from the optical detection unit 210. Namely, the optical volumes may increase in an order of an optical volume outputted from the top light sources 212 of the spaced distances S1, S2, and S3, and the optical volumes may be controlled by the optical volume control unit 111. Wavelengths of the lights from each of the top view light sources 212 may be identical to each other.

Also, the light source units 112 to be installed in a mobile terminal, including the top view light sources 212 and the guide units 211, may have a thickness of less than approximately 1.5 mm. As described above, a slimmer light source unit may be embodied by establishing at least two top view light sources in an array type to the guide unit 211. Accordingly, the optical sensor module 110 to be installed in the mobile terminal according to an embodiment of the present invention may be optimized, where a thickness is extremely limited due to a location of components within the mobile terminal.

Also, a slimmer, but comparatively greater surface light source may be embodied by arranging each of the top view light sources 212 in an array type in the guide units 211, regardless of thickness or a size of the mobile terminal.

Again referring to FIG. 1, the optical volume control 111 unit controls operational current supplied to the at least two top view light sources. As described above, the operation current may be controlled by optical volumes outputted from each of the top view light sources and may increase in proportion to the spaced distances from the optical detection unit 113.

The optical detection unit 113 receives at least two scattered lights from the measurement point 114 and transforms the received lights into an electrical signal. Namely, the optical detection unit 113 receives a light, irradiated from the light source unit 112 into the measurement point 114 and scattered from the measurement point 114, and transforms the received light into the electrical signal. For the above operation, the optical detection unit 113 may include an optical-electrical transducing element transforming an optical signal into an electrical signal.

The signal processing unit 120 receives the electrical signal and calculates a thickness of body fat in the measurement point 114. For the above operation, the signal processing unit 120 includes a signal amplification unit 121, a body fat information unit 122, and an output control unit 123

The signal amplification unit 121 transmits the received electrical signal to the body fat information unit 122 after amplifying the electrical signal which has been transformed in the optical detection unit 113.

The body fat information unit 122 calculates the thickness of the body fat in the measurement point 114 according to the amplified electrical signal. The body fat information unit 122 may calculate the thickness of the body fat from a strength of a scattered light, irradiated from the optical detection unit 112 and absorbed or scattered at the measurement point 114, and also calculates a body fat ratio as a percentage, or weight of the body fat via a reference lookup table. The above operation will be described below.

Figure 3:
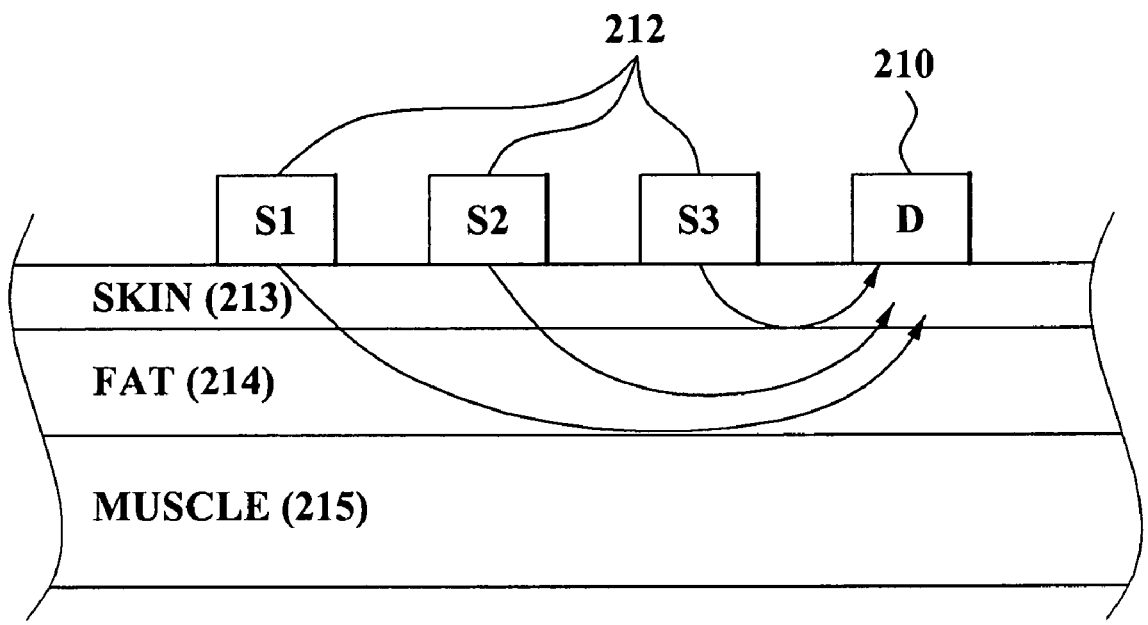
FIG. 3 is a diagram illustrating a side view of an optical sensor module in a portable body fat measurement device according to an embodiment of the present invention.

FIG. 3 is a diagram illustrating a lateral face of an optical sensor module in a portable body fat measurement device according to an embodiment of the present invention. Each of the light source units S1, S2, and S3 212 is horizontally arranged apart from the optical detection unit D 210 by spaced distances and supply light that is scattered by skin 213, fat 214 and muscle 215 and inputted to the detection unit D 210.

FIG. 4 illustrates histograms showing a relative volume of operation current of an optical sensor module and a relative volume of a scattered light scattered from a measurement point 114 according to an embodiment of the present invention.

As described in FIG. 2(a), each of the light source units S1, S2, and S3 is horizontally arranged apart from the optical detection unit D 210 by spaced distances SD1, SD2, and SD3. An optical volume control unit 111 may control the operation current supplied to each of the light source units S1, S2 and S3, as optical volumes become greater in an order of spaced distances from the optical detection unit D, i.e., an optical volume supplied to the light source unit S1 is greater than an optical volume supplied to the light source unit S2, and the optical volume supplied to the light source unit S2 is greater than an optical volume supplied to the light source unit S3.

In this case, as illustrated in FIG. 4, a volume of a scattered light, irradiated from the light source unit S1, scattered from the measurement point 114 and inputted to the detection unit D 210 is less than a scattered light corresponding to the light source unit S2, and a volume of the scattered light corresponding to the light source unit S2 is less than a scattered light corresponding to a light source unit S3.

Referring back to FIG. 1, an output control unit 123 controls the body fat information to be displayed or played via the output unit 130. The output unit 130 may display or play the body fat information via a display unit 131 or a sound output unit 132.

In this case, when the electrical signal transformed by the signal amplification unit 121 is less than a predetermined value, the output control unit 123 controls a message requesting a user to change a measurement point 114 to be displayed and/or played via the output unit 130. Specifically, when the body fat information calculation unit 122 is not able to calculate thickness of body fat since the electrical signal is weak, the output control unit 123 provides the user with the message requesting a change of the measurement point 114 via the output unit 130.

Referring to FIG. 1, when a blood vessel (not shown) is located at the measurement point 114, the electrical signal is weak. Blood flowing through the blood vessel (not shown) includes hemoglobin (Hb). The Hb has a property that causes absorption of the scattered light irradiated to the optical detection unit 113, i.e., since the Hb absorbs the scattered light, a volume of the scattered light irradiated to the optical detection unit 113 decreases, and in this case, the body fat may not be accurately measured.

Accordingly, when a volume of the electrical signal is less than the predetermined value, the output control unit 123 may provide the user with a message requesting a change of the measurement point 114. The message may be displayed in a display unit 131 in a type of a short message service (SMS) or played via the output unit 132 that utilizes an alerting sound or a speech message.

According to another embodiment of the present invention, in order to detect a case that the scattered light is absorbed in the Hb, at least one of the at least two top view light sources side-view light sources may output a light having a wavelength of approximately 600 through 800 nms, which has a comparatively greater absorption for the Hb.

Figure 5:
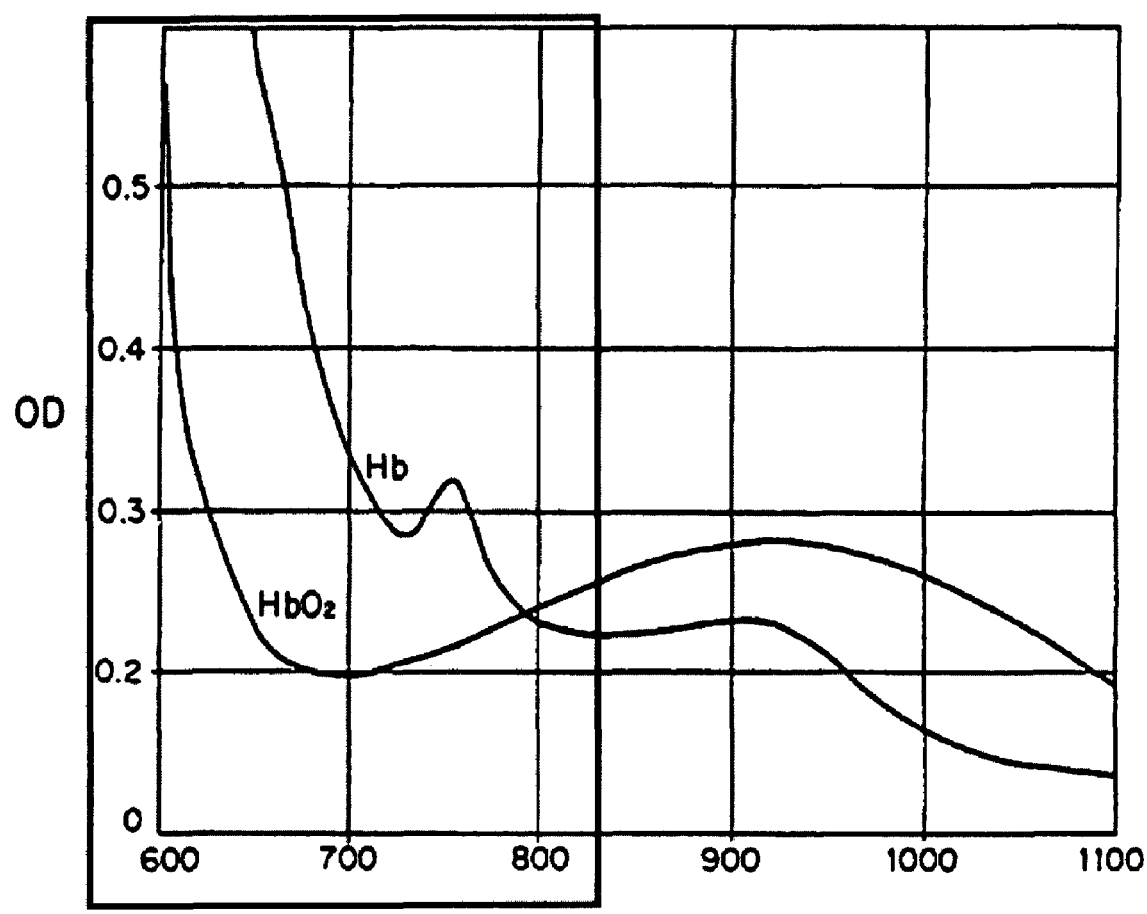
FIG. 5 is a diagram illustrating a decrease of absorption for each wavelength of a hemoglobin (Hb) component in blood according to an embodiment of the present invention.

FIG. 5 is a diagram illustrating a decrease of absorption for each wavelength of a Hb component in blood according to an embodiment of the present invention.

As illustrated in FIG. 5, absorption by the Hb for a wavelength between approximately 600 and 800 nm is highest. A guide unit 421 guides light that is irradiated from the light source units S1, S2 and S3 422. Accordingly, a case that an optical detection unit D 410 is located above a blood vessel is more accurately detected when at least one of the at least two light sources irradiates the light having the wavelength of approximately 600 through 800 nm, and subsequently a user is able to request a change of the measurement point 114. Namely, according to an embodiment of the present invention, a plurality of light sources may irradiate a light having a wavelength between approximately 600 and 950 nm, and more specifically, at least one of the plurality of light sources may irradiate a light having a wavelength between approximately 600 and 800 nm.

Accordingly to another embodiment of the present invention, a measurement error of thickness of body fat may be minimized since the portable body fat measurement device 100 is not located above the blood vessel of the user.

According to the present invention, there is provided a portable body fat measurement device and an optical sensor module in the device which may be installed in a portable terminal, e.g., a mobile communication terminal, by minimizing a thickness of the optical sensor module since a top view light source type light of a surface mount is used as the optical sensor module.

According to the present invention, there is provided a portable body fat measurement device and an optical sensor module in the device which minimize a thickness of the optical sensor module and enable sufficient optical volume for measuring a thickness of body fat since the optical sensor module is configured by horizontally arranging at least two light sources and an optical detection unit.

According to the present invention, there is provided a portable body fat measurement device and an optical sensor module in the device which minimize a decrease of optical power since an irradiation angle of a light outputted from a top view light source is limited via a guide unit, e.g., a prism sheet and the like, so that the light is perpendicularly irradiated in a measurement point.

According to the present invention, there is provided a portable body fat measurement device and an optical sensor module in the device which minimize a measurement error of a thickness of body fat which is caused by absorption of a scattered light by hemoglobin (Hb) by outputting a message requesting a change in a measurement point when an optical detection unit receiving a scattered light backscattered from the measurement point is above a blood vessel.

Although a few embodiments have been shown and described, it would be appreciated by those skilled in the art that changes may be made in these embodiments without departing from the principles and spirit of the invention, the scope of which is defined in the claims and their equivalents.

What is claimed is:

1. A portable body fat measurement device comprising:
   a plurality of light source units, each having at least two light sources arranged horizontally adjacent with respect to one another and a guide unit guiding an optical signal generated in the light sources to determine a measurement point where body fat is measured;
   an optical detection unit detecting a scattered optical signal to transform into an electrical signal, the scattered optical signal being generated by a scattering of the optical signal irradiated to the measurement point; and
   a signal processing unit processing the electrical signal and calculating body fat information,
   wherein the plurality of light source units are spaced apart at different distances from the optical detection unit, and a volume of light respectively outputted from the plurality of light source units increases as the respective distances between the optical detection unit and the plurality of light source units increase.

2. The device of claim 1, wherein the guide unit is a prism sheet.

3. The device of claim 1, further comprising:
   an optical volume control unit controlling an operation current to be supplied to the plurality of light source units.

4. The device of claim 1, wherein each of the at least two light sources is one of a point light source or a surface light source, and each of the at least two light sources includes a light emitting diode (LED).

5. The device of claim 1, wherein the signal processing unit comprises:
   a signal amplification unit amplifying an electrical signal, the electrical signal being transformed in the optical detection unit;
   a body fat information unit calculating body fat information from the amplified electrical signal; and
   an output control unit controlling the body fat information to be outputted in a predetermined display unit or sound output unit.

6. The device of claim 5, wherein the output control unit, when a strength of the electrical signal is less than a predetermined value, controls an output of a message request to change the measurement point via the display unit or sound output unit.

7. The device of claim 1, wherein at least one light source unit outputs an optical signal having a wavelength between approximately 600 and 800 nm.

8. The device of claim 1, wherein the portable body fat measurement device includes a mobile terminal.

9. The device of claim 8, wherein the mobile terminal is one of a personal digital assistant (PDA), a portable game device, an MP3 player, a personal multimedia player (PMP), a Digital Multimedia broadcasting (DMB) terminal, or a notebook.

10. The device of claim 1, wherein the optical detection unit comprises an optical-electrical transducing element transforming an optical signal into an electrical signal.

11. The device of claim 1, wherein at least one light source unit outputs a light having a wavelength between approximately 600 and 950 nm.

12. The portable body fat measurement device of claim 1, wherein the optical detection unit is arranged horizontally with the at least two light sources.

13. An optical sensor module included in a body fat measurement device, the module comprising:
   a plurality of light source units, each having at least two light sources arranged horizontally adjacent with respect to one another and a guide unit guiding an optical signal generated in the light sources to determine a measurement point wherein body fat is measured;
   an optical detection unit detecting a scattered optical signal to transform into an electrical signal; and
   a signal processing unit receiving the electrical signal to calculate body fat information at the measurement point,
   wherein the plurality of light source units are at different distances from the optical detection unit, and a volume of light respectively outputted from the plurality of light source units increases as the respective distances between the optical detection unit and the plurality of light source units increase.

14. The optical sensor module of claim 13, wherein the guide unit is a prism sheet.

15. The optical sensor module of claim 13, the module further comprising:
   an optical volume control unit controlling an operation current supplied to the plurality of light source units.

16. The optical sensor module of claim 13, wherein the at least two light sources are one of an LED point light source or an LED surface light source.

17. The optical sensor module of claim 13, wherein the optical detection unit comprises an optical-electrical transducing element transforming an optical signal into an electrical signal.

18. The optical sensor module of claim 13, wherein at least one light source unit outputs an optical signal having a wavelength between approximately 600 and 800 nm.

19. The optical sensor module of claim 13, wherein at least one light source unit outputs an optical signal having a wavelength between approximately 600 and 950 nm.

* * * * *

UNITED STATES PATENT AND TRADEMARK OFFICE
CERTIFICATE OF CORRECTION

| | |
|---|---|
| PATENT NO. | : 7,805,184 B2 |
| APPLICATION NO. | : 11/797199 |
| DATED | : September 28, 2010 |
| INVENTOR(S) | : In Duk Hwang et al. |

It is certified that error appears in the above-identified patent and that said Letters Patent is hereby corrected as shown below:

Column 9, line 4, in claim 12, after "The" delete "portable body fat measurement".

Signed and Sealed this
Fourth Day of January, 2011

David J. Kappos
*Director of the United States Patent and Trademark Office*